United States Patent [19]

Issalene et al.

[11] Patent Number: 4,872,837
[45] Date of Patent: Oct. 10, 1989

[54] SURGICAL OR DENTAL INSTRUMENT AND CANNULAE FOR ASPIRATING, CLEANING, DRYING AND ILLUMINATING

[76] Inventors: Robert Issalene, 7, rue Ampère, 83100 Toulon; Jean-François Lantrua, "La Campagne" Lot. les Grés Macany, 83400 Hyeres, both of France

[21] Appl. No.: 151,537
[22] Filed: Feb. 3, 1988

[30] Foreign Application Priority Data
Feb. 6, 1987 [FR] France ................. 87 01569

[51] Int. Cl.[4] ................. A61C 3/00; A61C 17/02; A61C 17/04
[52] U.S. Cl. ................. 433/29; 433/80; 433/91; 604/902
[58] Field of Search ........ 433/29, 91, 80, 84, 433/85, 126; 604/902

[56] References Cited
U.S. PATENT DOCUMENTS

| | | | |
|---|---|---|---|
| 2,709,852 | 6/1955 | Maurer et al. | 433/29 |
| 4,617,013 | 10/1986 | Betz | 604/902 |
| 4,619,612 | 10/1986 | Weber et al. | 433/29 |
| 4,629,425 | 12/1986 | Detsch | 433/29 |
| 4,648,838 | 3/1987 | Schlachter | 433/29 |
| 4,743,199 | 5/1988 | Weber et al. | 433/80 |

Primary Examiner—John J. Wilson
Attorney, Agent, or Firm—Marshall & Melhorn

[57] ABSTRACT

This invention relates to a surgical or dental instrument capable of illuminating, washing with liquid, washing with sprayed liquid, drying with air, and aspirating. The instrument incorporates a hollow body comprising means for connecting it to a suction tube, means for fitting thereto a removable cannula, means for supplying fluids which will be conveyed to the end of the cannula, and a supply of electrical current for illuminating a bulb. The hollow body contains a sleeve traversed by an axial bore whose diameter is equal to the inner diameter of the cannula. The sleeve includes, a housing in which is placed a bulb which emits light in the direction of the cannula. The cannula is shaped and positioned for the light generated by the bulb to be conveyed in the sleeve then in the cannula, whose wall performs the role of light conductor. The cannula further includes conduits for conveying fluids. The cannula and the hollow body are shaped so that the cannula may pivot on itself in the hollow body.

5 Claims, 4 Drawing Sheets

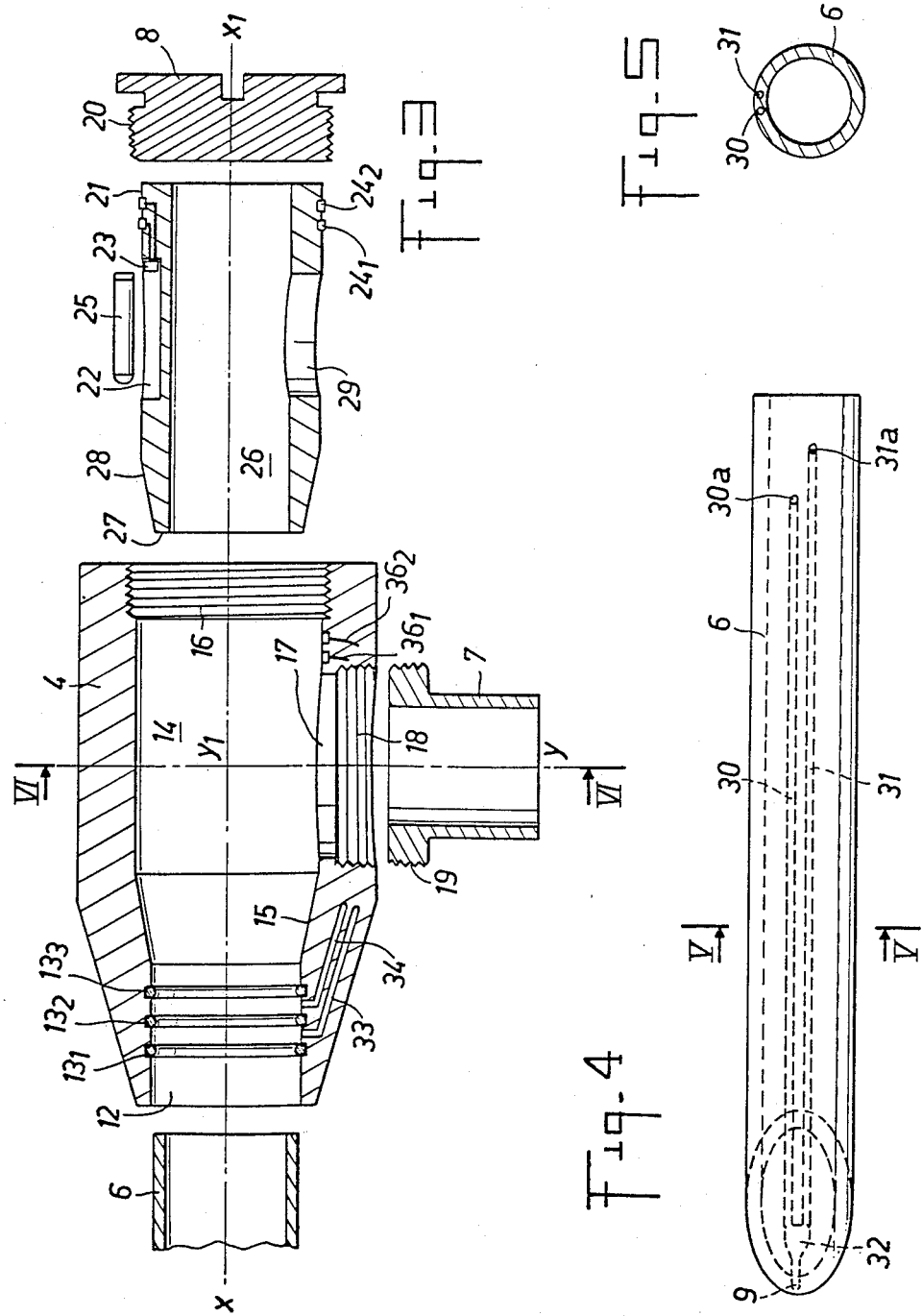

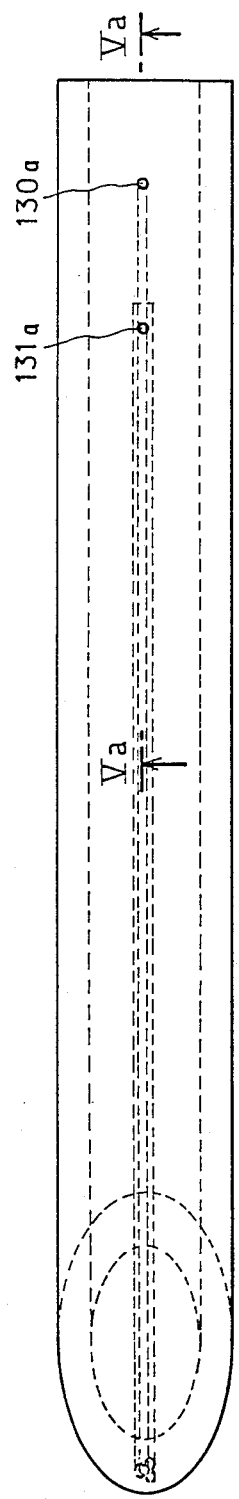
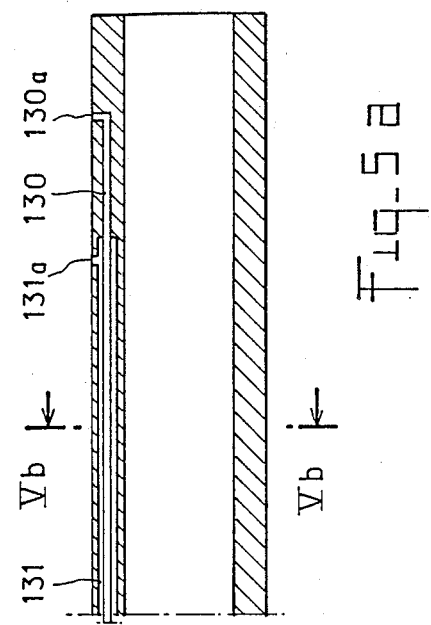
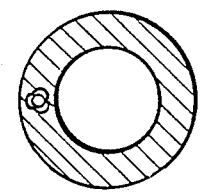
Fig. 4a
Fig. 5a
Fig. 5b

SURGICAL OR DENTAL INSTRUMENT AND CANNULAE FOR ASPIRATING, CLEANING, DRYING AND ILLUMINATING

FIELD OF THE INVENTION

The present invention relates to surgical and dental instruments and to cannulae intended for aspirating, cleaning, drying and illuminating.

The technical sector of the invention is that of the construction of surgical, and particularly dental apparatus.

BACKGROUND OF THE INVENTION

Dental installations often comprise cannula holders which are fixed to the end of a pipe connected to a suction means and on which is fitted a suction cannula, which is disposable or sterilizable, whose end is introduced into the mouth in order to suck out the liquids and debris.

Suction instruments placed in the mouth are known, which are combined with cleaning means which send a stream of atomized water or a jet of air into the mouth.

Dental instruments for cleaning are also known, which are associated with an optical fiber which illuminates the interior of the mouth U.S. Pat. No. 3,727,310 to Baker describes suction cannulae for dental use which comprise a hollow cannula in the form of a pistol grip equipped with a longitudinal conduit maintained under depression and, in addition, with two small conduits which are housed in the wall of the cannula and which convey water and compressed air, respectively. The cannula comprises a removable nozzle.

European Patent Application No. 138,119 Siemens describes a dental spray grip which comprises a bent grip on which is fitted a removable nozzle which may rotate slightly on its axis.

The grip comprises air and water conduits and electrical conductors which supply an electric lamp placed at the center of a bore in which the removable nozzle is fitted.

The removable nozzle comprises an axial conduit which conveys air. It comprises a small conduit which conveys water, of which the front end is disposed at the center of the axial air conduit. It comprises a light conductor which is disposed at the center of the rear part of the axial air conductor and on the periphery of the front, end thereof.

The instrument described in the patent to Siemens is a cleaning apparatus which does not aspirate, European Patent Application No. 022,150 to Pisanu describes an instrument for cleaning by spraying and suction intended more particularly for dental care. This instrument is connected to a grip which is placed at the end of a flexible suction tube. It comprises a bent or straight suction cannula . It comprises a small tube housed inside the suction conduit of the cannula and at the center of the distal end thereof. This tube may convey air, a liquid or a mixture of the two.

The cannula which is connected to the small tube conveying the mixture of air and water cannot rotate about its axis.

French Pat. No. 449,995 to Firma et al. describes instruments which may be introduced into cavities in the human body and which comprise two tubes between which are disposed optical fibers for illuminating the operative field. The central tube may serve to aspirate foreign bodies, to introduce a handling device or to inject a liquid or a gas.

U.S. Pat. No. 3,208,145 describes suction instruments for dental use comprising two small air and water tubes, placed outside the instrument.

U.S. Pat. No. 3,624,907 Brass et al. describes dental instruments intended for cleaning the tooth root canals. These instruments comprise at their end a needle for injection of liquid which is placed at the centre of a suction nozzle.

The problem that the invention is seeking to solve is that of providing suction-cannula -holder instruments which can be fitted on the standard cannula -holders often equipping dental surgeries and which may receive suction cannulae comprising means for illuminating the interior of the mouth, means for washing by a stream of water, atomized or not, and drying means incorporated in the cannula which leave the suction canal of the cannula free and which do not hinder the freedom of the latter to pivot about its axis.

SUMMARY OF THE INVENTION

The solution, according to the present invention, for solving the problem raised consists in a dental instrument comprising a hollow body incorporating means for connecting it to a suction pipe, means for fitting thereon a removable cannula , means for supplying fluids which will be conveyed to the end of said cannula , and a supply of electrical current for illuminating a bulb.

The said hollow body contains a sleeve, made of a transparent material having a refraction coefficient greater than that of air, traversed by an axial bore those diameter is equal to the inner diameter of the cannula. The sleeve comprises on its periphery, a housing in which is placed the bulb which emits light in the direction of the cannula.

The cannula is made of a transparent material having a refraction coefficient greater than that of air, the rear end of the cannula is, when the cannula is fitted in the hollow body, in contact with the front end of said sleeve, so that the light generated by the bulb is conveyed in the sleeve then in the cannula where the wall performs the role of light conductor. The cannula also includes in its wall longitudinal conduits for transporting the fluids. The conduits open out, on the one hand, possibly via a mixing chamber and an orifice, at the outer end of the cannula and, on the other hand, in the vicinity of the other end of the cannula on the outer wall of the cannula at two points which are offset longitudinally and which communicate with spaces disposed between spaced O-rings arranged in the inner face of the hollow body, into which the ends of the means for supplying the fluids also open out.

the cannula and the hollow body are at the level of those parts of these pieces corresponding to the fit, of cylindrical section, so that the cannula may pivot on itself in the hollow body.

BRIEF DESCRIPTION OF THE DRAWINGS

The invention will be more readily understood on reading the following description with reference to the accompanying drawings, in which:

FIG. 3 is an exploded axial section of an instrument according to the invention.

FIGS. 4 and 5 are views in plan and in transverse section of a cannula according to a first embodiment of the invention.

FIGS. 4a and 5b are views similar to FIGS. 4 and 5 of a cannula according to a second embodiment of the invention, FIG. 5a being a partial view in axial section along Va—Va of FIG. 5.

DETAILED DESCRIPTION OF THE DRAWINGS

Figure 1:
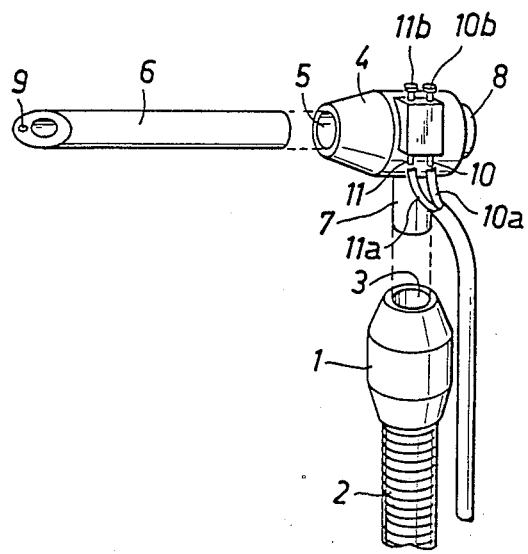
FIGS. 1 and 2 represent views in perspective of two possible uses of an instrument according to the invention.
Figure 2:
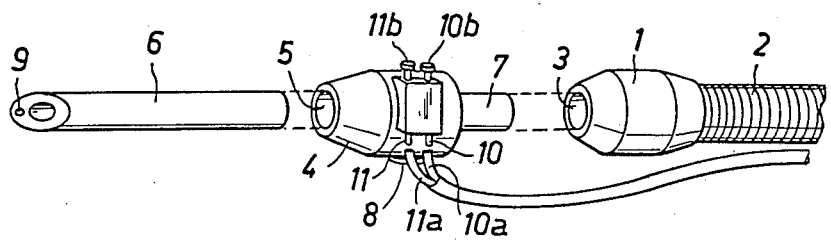

Referring now to the drawings, FIGS. 1 and 2 show a cannula-holder 1 which is fixed to the end of a suction tube 2, i.e. a tube which is connected to any suction means. Such cannula-holders often equip dental care installations. The cannula-holder comprises, at its front end, a bore 3, in which are conventionally fitted suction cannulae which are disposable after use or sterilizable, which cannulae serve to suck liquids and debris from inside the mouth.

An instrument according to the invention comprises a hollow body 4 which comprises, at its front end, a bore 5, in which may be fitted, in substantially tight manner, a suction cannula 6. The hollow body is traversed right through by a canal which causes the interior of the cannula to communicate with the flexible suction tube 2.

The hollow body 4 is equipped with a removable connecting piece 7 which comprises an endpiece whose outer diameter corresponds to that of the cannulae, with the result that this endpiece may be fitted in the bore 3 of a conventional cannula-holder 1.

The connecting piece 7 may occupy two different positions on the hollow body 4. To that end, the hollow body 4 comprises two identical circular orifices, each provided with a female thread: a first axial orifice which is located at the rear end of the hollow body 4 and which is centered on the longitudinal axis of the hollow body 4 and a second orifice which is located on the lateral wall of the body 4 and whose axis is perpendicular to the longitudinal axis of the body 4.

The hollow body 4 may also be equipped with a threaded stopper 8 which may be screwed on one or the other of the two threaded orifices mentioned above.

FIG. 1 shows a first assembly in which the connecting piece 7, which is threaded, is screwed on the lateral orifice, whilst the axial orifice is obturated by the threaded stopper. In that case, the body 4 forms with the cannula-holder 1 a pistol grip.

FIG. 2 shows a second assembly in which the body 4 is disposed in line with the cannula-holder 1, the connecting piece 7 being screwed on the axial orifice, whilst the stopper 8 is screwed on the lateral orifice.

The cannulae 6 according to the invention are made of a transparent material having a refraction coefficient greater than one, for example polycarbonate. This material can withstand temperatures which may attain 150° C., which makes it possible to sterilize the cannulae by heating. The front end of the cannulae 6 are bevelled.

The hollow body 4 contains a small electric lamp and means for directing in a substantially axial direction the light emitted by the lamp and which concentrate this light on the ring of transparent material which constitutes the rear end of the cannula 6, which is fitted in the hollow body 4.

The light penetrates in the wall of the cannula and is channelled towards the front end of the cannula.

As the material has a refraction coefficient greater than one and the light has a substantially axial direction, the light undergoes total reflections on the inner and outer faces of the cannula. Thus, the material forms a light conduit and it emerges at the front end in the form of an annular beam of light, concentric with the cannula, hence a very good illumination of the zone towards which the cannula is directed.

A cannula 6 according to the invention comprises two small longitudinal conduits or canals for conveying fluid, opening, on the one hand, at the outer end of the cannula, and on the other hand, in the vicinity of the other end of the cannula where they are each connected to a source of fluid supply. One of the conduits conveys for example water or a liquid, whilst the other conveys air or a compressed gas. These fluids may be sent either separately or simultaneously in order to produce a jet of atomized liquid.

These fluid conveying conduits are generally in the form of capillary tubes embedded in the wall of the cannula or of small canals hollowed in this wall. In this way, the central canal which traverses the cannula 6 and forms part of the path of suction is free of any obstacle.

The hollow body 4 comprises two endpieces 10 and 11 on each of which is connected a small flexible tube 10a and 11a, conveying respectively a liquid and a gas or a powder in suspension in a gas. Each endpiece 10 and 11 communicates with a valve with plunger piston 10b and 11b which comprises a maneuvering head which may be maneuvered with the fingers by the practician who holds in one hand the grip 1 bearing an instrument according to the invention. This maneuver is possible in the two assemblies shown in FIGS. 1 and 2.

FIG. 3 is an exploded view in axial section of an instrument according to the presently preferred embodiment of the invention.

This Figure shows the hollow body 4 which has a cylindro-conical form of axis x-$x_1$, the rear end of a cannula 6, a connecting piece 7 and a stopper 8.

The hollow body 4 comprises, at the front end, a cylindrical bore 12 of which the inner diameter is slightly greater than the outer diameter of the cannulae 6.

The bore 12 comprises three peripheral grooves $13_1$, $13_2$ and $13_3$ which each receive an O-ring which serves as a seal for the cannula 6 which is engaged in the bore 12.

The hollow body 4 further comprises a cylindrical counter-bore 14 whose diameter is larger than that of the bore 12. The counter-bore 14 is connected to bore 12 by a truncated bore 15.

Bores 12, 14, 15 form a canal of axis x-$x_l$ which passes right through the hollow body 4.

Bore 14 opens out at the rear end of the hollow body 4 via an orifice which comprises a female thread 16.

The hollow body 4 comprises a radial canal 17 which opens out in bore 14. This canal opens to the outside via a lateral orifice which comprises a female thread 18. Threads 16 and 18 are identical.

The connecting piece 7 comprises a cylindrical endpiece whose outer diameter is identical to the diameter of the cannulae 6, with the result that this endpiece may be fitted in a standard cannula-holder. The connecting piece 7 further comprises a male thread 19 which may be screwed in the threads 16 or 18.

An instrument according to the invention comprises a stopper 8 provided with a male thread 20 which may also screw in one of the threads 16 or 18.

Merely by way of illustration, FIG. 3 shows a connecting piece 7 in the lateral threaded orifice 18 and a stopper 8 in the rear threaded orifice 16, but the reverse is also possible.

The hollow body 4 further contains an intermediate piece 21 which has the form of a cylindro-conical sleeve. This sleeve is made of a transparent material having a high refraction coefficient, for example polycarbonate.

The sleeve 21 comprises, on its periphery, an outer housing 22 made in the wall of the sleeve, and adapted to receive a small bulb 25.

At the rear end of the housing 22, there is provided a socket 23 which is connected to two electricity conducting rings $24_1$ and $24_2$ housed in two peripheral grooves in the sleeve. The bulb 25 is plugged in the socket 23 and emits a ray of light forwardly, in the direction of the cannula.

The sleeve 21 is traversed right through by an axial bore 26 of which the inner diameter is equal to the inner diameter of the cannulae 6.

The front end of the sleeve 21 comprises a radial surface 27 in the form of a ring whose width is equal to the thickness of the walls of the cannula 6.

The front end of the sleeve 21 further comprises a truncated surface 28 which converges towards the radial surface and whose aperture angle is the same as that of the truncated bore 15 against which it abuts when the sleeve is placed inside the hollow body.

In this position, the ring 27 is placed in contact with the crown of transparent material forming the rear end of the cannula 6 and said crown and said ring merge, i.e. they are perfectly superposed.

Being given that the bulb is located outside the bore of the sleeve 21 and that this bore corresponds exactly to the central canal of the cannula 6, there is no obstacle on the path of suction inside the instrument according to the invention.

This conformation is particularly advantageous since it avoids the risk of particles being deposited inside the instrument, and consequently the necessity of frequent cleanings.

The sleeve 21 comprises at the rear a cylindrical body of which the outer diameter is slightly less than the diameter of the bore 14, in which it is engaged, with the result that the intermediate piece may be engaged inside the hollow body or extracted therefrom through the threaded orifice 16.

The sleeve 21 comprises a radial canal 29 which is positioned opposite the lateral canal 17, when the sleeve is engaged in the hollow body 4.

A cannula 6 according to the invention is made of a transparent material, for example polycarbonate, in the form of a portion of tube having the dimensions of conventional suction cannulae.

The front end of the cannula is bevelled in the known manner and it is perfectly polished, as is the rear end of the cannula. The bevel shape will be chosen so as to enable the light to be concentrated and directed in a controlled manner where desired.

As previously, the cannula comprises, in its wall, two longitudinal conduits for conveying fluid, the conduits opening out on the one hand at the outer end of the cannula, on the other hand in the vicinity of the other end of the cannula on the outer wall of the cannula, at points which are offset longitudinally and which communicate with spaces formed between the O-rings $13_1$, $13_2$, $13_3$ arranged in the inner face of the hollow body 4 into which fluid supply means which will be described hereinafter likewise open out.

FIGS. 4 and 5 show a first embodiment of a cannula according to the invention. As is seen, the two longitudinal conduits 30, 31 extend in the wall of the cannula 6, along the generatrix which terminates at the front-most point of the bevelled end.

At their front end, the conduits 30, 31 join each other in a mixing chamber 32 which comprises an orifice 9 opening out at the front-most point of the bevelled end.

The rear ends of the two conduits open out radially outwardly through two orifices 30a and 31a which are offset longitudinally.

Orifice 31a is positioned between the two O-rings placed in grooves $13_2$ and $13_3$, whilst orifice 30a is positioned between the O-rings placed in grooves $13_1$ and $13_2$.

FIG. 3 shows two small fluid supply canals 33 and 34 which are hollowed in the mass of the hollow body 4 and which open out in the bore 12, one between grooves $13_1$ and $13_2$ and the other between grooves $13_2$ and $13_3$.

FIGS. 4a, 5a and 5b show a second, preferred, embodiment of a cannula according to the invention.

Conduits 130, 131, likewise made in the wall of the cannula 6, are here concentric. The water or liquid will preferably be made to circulate in the central conduit and the air or gas in the peripheral conduit.

The peripheral conduit 131, at its front end which terminates at the front-most point of the bevelled end, will preferably be gripped and crushed for example with the aid of a triangular mandrel, which allows an automatic centering of this conduit on the central conduit. Such conformation also makes it possible to increase the speed of the air or compressed gas emerging from the peripheral conduit.

At their rear end, the two conduits open out radially outwardly via two orifices 130a and 131a which are longitudinally offset and axially aligned. Their role and functioning are strictly similar to those of orifices 30a and 31a.

Figure 6:
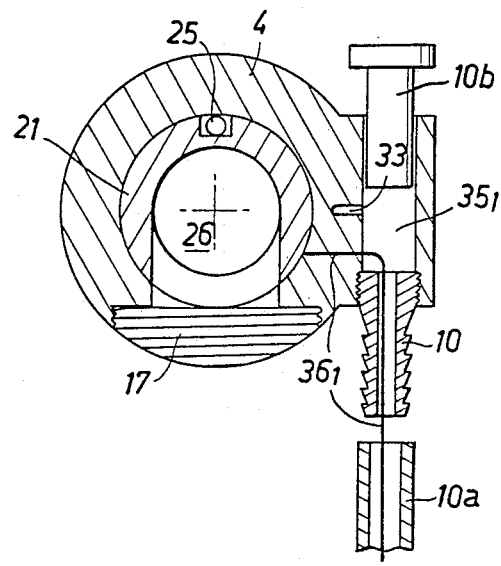
FIG. 6 is a transverse section along VI—VI of FIG. 3.

FIG. 6 shows a transverse section along VI—VI of the hollow body 4 shown in FIG. 2. The transparent sleeve 21 is shown in position inside the hollow body 4.

The hollow body 4 comprises a lateral appendix in which are hollowed two vertical cylindrical chambers 35 of which only one, $35_1$, is visible in FIG. 6. Each chamber 35 communicates with one of the canals 33 or 34 hollowed in the mass of the body.

Each chamber 35 comprises, in its lower part, a connection such as connection 10, comprising a fluted endpiece on which is connected a small flexible tube such as tube 10a, conveying a liquid and a gas respectively.

Each chamber is equipped in its upper part with a valve 10b composed of a plunger piston which is engaged in the chamber and which is provided with a maneuvering head on which the practician presses with his thumb to adjust the flowrate of water or air.

A conducting wire 36, preferably made of stainless steel, which is connected to one of the terminals of a D.C. source of low-voltage (3 to 3 volts), is the tubes 10a which serves at the same time as insulating sheath.

Each wire 36₁ or 36₂ passes through the mass of the hollow body 4 and projects inside the axial bore 14 in a position such that it comes into contact with one of the conducting rings 24₁ or 24₂ located on the periphery of the sleeve 21, which enables the lamp 25 to be supplied.

Although the cannulae have been shown rectilinear in the Figures, it is specified that an instrument according to the invention may also receive bent cannulae which may be oriented in any position thanks to the total freedom of sealed rotation of the cannula about its axis.

In summary, the principal advantages of the dental apparatus according to the invention are enunciated below.

They may fit on standard suction-cannula-holders which conveniently equip dentists' surgeries without having to modify them. It suffices to add to the suction tube a sheath containing two air and water conduits in each of which passes a conducting wire connected to a low-voltage source.

The devices according to the invention may be mounted in line with the cannula-holder or the latter may be used as pistol grip.

The special cannulae adaptable to the devices according to the invention simultaneously ensure the functions of suction, of water and air supply, therefore of cleaning and drying, and also of illumination inside the mouth.

This result is attained without introducing any obstacle in the suction canal, with the result that the latter conserves optimum efficiency and the suction cannula may be oriented in any direction, since it may pivot freely about its axis.

The cannulae according to the invention are easily interchangeable since it suffices to fit them in the body of the apparatus. They may be sterilized or even discarded after use as their manufacturing costs are relatively low. They may be mass produced by extrusion or moulding.

The illumination obtained by the cannulae according to the invention, which act as light conduit, makes it possible to obtain at the distal end of the cannula a ring of light which illuminates the zones towards which the cannula is directed without dazzling the practician, as the light emerging from the cannula forms a forwardly directed annular beam.

The intermediate piece in the form of a transparent sleeve 21 which equips the apparatus according to the invention may easily be extracted from the body by the rear end thereof, which allows complete dismantling of the apparatus to clean it.

Figure 7:
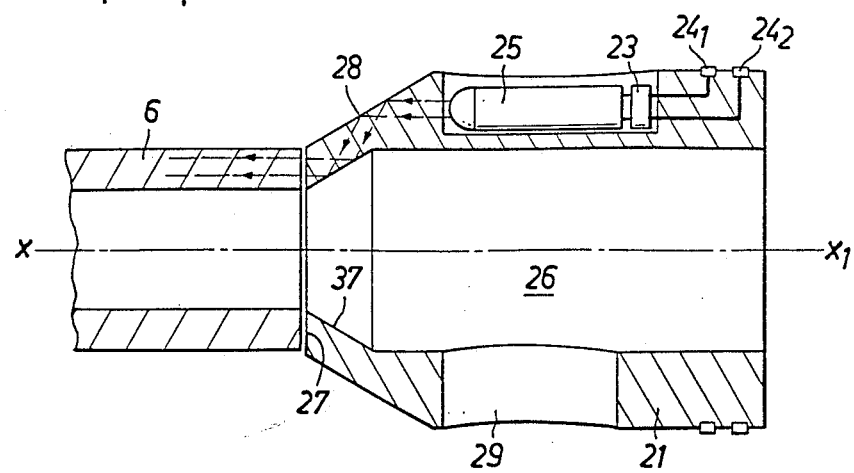
FIG. 7 is an axial section of a variant embodiment of the transparent sleeve.

FIG. 7 is an axial section of a variant embodiment of the transparent sleeve 21 equipping an instrument according to the invention.

In this variant, the outer wall of the front end of the sleeve presents a conical surface 28 which converges forwardly and the inner bore of the sleeve 26 likewise presents, at the front end, a conical inner surface 37 which is substantially parallel to the conical outer surface 28, with the result that the rays emitted by the lamp 25 in a direction substantially parallel to the axis are reflected on the two substantially parallel faces 28 and 37 and enter the material of the cannula 6 with a substantially axial direction.

The instrument which has just been described essentially finds application in the dental domain.

However, as will be readily understood, it may also be used in surgery, subject to slight modifications which in no way modify the basic principle thereof.

What is claimed is:

1. A surgical or dental instrument comprising a hollow body incorporating means for connecting it to a suction pipe, means for fitting thereon a removable cannula, means for supplying fluid which will be conveyed to the end of said cannula, and a supply of electrical current for illuminating a bulb, wherein said hollow body contains a sleeve, made of a transparent material having a refraction coefficient greater than that of air, traversed by an axial bore whose diameter is equal to the inner diameter of said cannula, said sleeve comprising, on its periphery, a housing in which is placed said bulb which emits light in the direction of said cannula, said cannula being removably connected to said hollow body;

said cannula is made of a transparent material having a refraction coefficient greater than that of air, the rear end of said cannulae is, when said cannula is fitted in said hollow body, in contact with the front end of said sleeve, so that the light generated by said bulb is conveyed in said sleeve then in said cannula of which the wall performs the role of light conductor; said cannula further comprising in its wall longitudinal conduits for transporting said fluids, said conduits opening out, on the one hand, at the outer end of said cannula and, on the other hand, in the vicinity of the other end of the cannula on the outer wall of said cannula at two points which are offset longitudinally and which communicates with spaces disposed between spaced O-rings arranged in the inner face of said hollow body, into which the ends of the means for supplying said fluids also open out;

said cannula and said hollow body being at the level of those parts of these pieces corresponding to the fit, of cylindrical section, so that said cannula may pivot on itself in said hollow body.

2. The instrument of claim 1, wherein said hollow body comprises two orifices located, one, at the rear end and, the other, on the lateral wall of said hollow body and it further comprises a threaded stopper which screws on one of the two orifices and a threaded endpiece which is screwed on the second orifice, with the result that said hollow body may be placed in line with a cannula-holder when the threaded endpiece is screwed on the rear orifice, or form a pistol grip with a cannula-holder when said threaded endpiece is screwed on the lateral orifice.

3. The instrument of either one of claims 1 and 2, wherein it comprises two valves with plunger piston provided with a maneuvering knob which are each placed in a cylindrical chamber which communicates with one of said liquid or gas conduits and which comprises a connection on each of which is connected a small tube of plastics material connected respectively to a source of liquid and to a source of compressed gas and each of the two tubes contains an electric conductor which is connected to a source of low-voltage current, which conductors supply said lamp.

4. The instrument defined in claim 1, wherein the outer end of said cannula is bevelled allowing correct use of the light conveyed by said cannula, and the two longitudinal conduits are placed in the vicinity of the generatrix which terminates at the front most point of the outer end of said cannula and open out in a mixing chamber which opens out at the front end of said cannula by an orifice located near the front-most point of the bevelled end.

5. The instrument defined in claim 1, wherein said cannula includes two concentric longitudinal conduits for conveying fluid housed in the walls of said cannula.

* * * * *